(12) United States Patent
Vemalarajah

(10) Patent No.: US 9,352,314 B2
(45) Date of Patent: May 31, 2016

(54) SPECIMEN COLLECTING AND TESTING APPARATUS

(76) Inventor: Ratnarajah Vemalarajah, Selangor (MY)

( * ) Notice: Subject to any disclaimer, the term of this patent is extended or adjusted under 35 U.S.C. 154(b) by 0 days.

(21) Appl. No.: 13/514,430

(22) PCT Filed: Dec. 1, 2010

(86) PCT No.: PCT/MY2010/000315
§ 371 (c)(1),
(2), (4) Date: Jun. 7, 2012

(87) PCT Pub. No.: WO2011/071364
PCT Pub. Date: Jun. 16, 2011

(65) Prior Publication Data
US 2013/0006146 A1 Jan. 3, 2013

(30) Foreign Application Priority Data
Dec. 7, 2009 (MY) .............................. PI20095202

(51) Int. Cl.
| | | |
|---|---|---|
| *B65D 81/00* | (2006.01) | |
| *B01L 3/00* | (2006.01) | |
| *A61B 10/00* | (2006.01) | |
| *G01N 33/493* | (2006.01) | |
| *G01N 1/00* | (2006.01) | |

(52) U.S. Cl.
CPC .............. *B01L 3/5023* (2013.01); *A61B 10/007* (2013.01); *G01N 33/493* (2013.01); *A61B 10/0096* (2013.01); *A61B 2010/0009* (2013.01); *B01L 2200/025* (2013.01); *B01L 2200/141* (2013.01); *B01L 2300/042* (2013.01); *B01L 2300/0609* (2013.01); *B01L 2300/087* (2013.01); *B01L 2300/0832* (2013.01); *G01N 2001/007* (2013.01)

(58) Field of Classification Search
USPC .......... 4/144.1, 144.2, 144.3, 144.4; 600/573; 604/317, 321
See application file for complete search history.

(56) References Cited

U.S. PATENT DOCUMENTS

| | | | |
|---|---|---|---|
| 5,897,840 A * | 4/1999 | Owens et al. | ................. 422/559 |
| 6,277,646 B1 | 8/2001 | Guirguis et al. | |
| 6,379,620 B1 * | 4/2002 | Tydings et al. | ............... 422/412 |
| 7,244,392 B1 | 7/2007 | Konecke | |
| 7,270,959 B2 | 9/2007 | Hudak | |
| 7,517,495 B2 | 4/2009 | Wu et al. | |
| 8,048,321 B2 * | 11/2011 | Leach et al. | .................. 210/782 |

(Continued)

OTHER PUBLICATIONS

International Search Report and Written Opinion for International application No. PCT/MY2010/000315, dated Sep. 16, 2011 (6 pages).

(Continued)

*Primary Examiner* — Sean Dougherty
*Assistant Examiner* — Daniel Cerioni
(74) *Attorney, Agent, or Firm* — Wolf, Greenfield & Sacks, P.C.

(57) ABSTRACT

The present invention relates to a specimen collecting and testing apparatus and a method for testing the specimen using said apparatus, and more particularly concerns a specimen and testing apparatus for collecting urine specimen use in drug screening program wherein said apparatus has tamper-proof features to prevent adulteration or substitution and a method of using the same. This apparatus also provides a novel arrangement for retaining the specimen collected having tamper-proof features and is also leak proof and easy to handle.

14 Claims, 5 Drawing Sheets

(56) References Cited

U.S. PATENT DOCUMENTS

| | | | |
|---|---|---|---|
| 8,246,552 B2 * | 8/2012 | Minassians | 600/573 |
| 2002/0085953 A1 * | 7/2002 | Parker | 422/61 |
| 2003/0021736 A1 * | 1/2003 | Kang et al. | 422/102 |
| 2003/0053938 A1 * | 3/2003 | Szeles | 422/102 |
| 2004/0132091 A1 | 7/2004 | Ramsey et al. | |

OTHER PUBLICATIONS

International Preliminary Report on Patentability for International application No. PCT/MY2010/000315, dated Jun. 12, 2012 (4 pages).

* cited by examiner

SPECIMEN COLLECTING AND TESTING APPARATUS

RELATED APPLICATION

This application is a national stage filing under 35 U.S.C. §371 of international application PCT/MY2010/000315, filed Dec. 1, 2010 which was published under PCT Article 21(2) in English.

TECHNICAL FIELD OF THE INVENTION

This present invention relates to a specimen collecting and testing apparatus and a method for testing the specimen using said apparatus, and more particularly concerns using the specimen collecting and testing apparatus to collect urine specimen for testing drug of abuse wherein said apparatus is leak proof and tamper-proof to prevent adulteration or substitution of the urine specimen after it has been collected and a method of using the same.

BACKGROUND OF THE INVENTION

The increase in drug use over the past several decades has created a sharp need for a more efficient, effective and quick method of analyzing as to whether a particular individual is a user of certain illegal substances or drug of abuse.

One of the easiest and most common test types is to require the person to supply a urine specimen for testing. The urine specimen can be used to determine the presence of certain illegal substances of drug of abuse for example amphetamines, methamphetamines, phencyclidines, cannabinoids, marijuana, cocaine, morphine, heroin, opiates and others.

Hence, there are many different types of urine drug test kits available as on-site tests, and/or laboratory analysis. If a positive result (drug presence indicated) is found, the specimen is usually sent to a laboratory for confirmation test. However, there are two main problems with regard to the use of urine drug test kits. First, the efficacy of urine testing is debatable due to systematic cheating. This may be done through simple adulteration or specimen substitution and both are effective ways of avoiding would-be positive tests. As such, to ensure that the urine specimen collected is not adulterated or substituted there may be a need to monitor the taking of urine specimen to ensure reliability of the test results. And direct monitoring of the collection of urine specimen in itself pose another problem of invading the privacy rights of the person. Secondly, there is a concern that there may be tampering with the urine specimen after is has been collected.

Further during the transfer of the specimen it may be that vigorous shaking of the container causes spillage of the specimen or backflow of the specimen. If the specimen should test "positive" to indicate the presence of a drug in the urine, it is then necessary to send the specimen for confirmatory test done in a certified laboratory. Additionally, the specimen could be spilled or contaminated if the lid or cap of the cup is removed for said confirmatory test. It is therefore necessary to make the containers leak proof and easy to handle under such situation.

There are many known testing devices or apparatus which were proposed for the collection of urine specimen. However, none have specially designed tamper-proof features to prevent adulteration or substitution of the specimen collected. Hence according to the present invention, the specimen collecting and testing apparatus provides this solution by providing tamper-proof features for collecting and testing urine specimen and preventing the specimen from being adulterated or substituted. In addition the said apparatus is leaf proof and easy to handle.

SUMMARY OF THE INVENTION

Accordingly, it is a primary object of the present invention to provide a specimen collecting and testing apparatus, particularly a urine collecting and testing apparatus having tamper-proof features to prevent adulteration or substitution for use in drug screening program.

Accordingly, it is another object of the present invention to provide a specimen collecting and testing apparatus that is leak proof and easy to handle.

Accordingly, it is another object of the present invention to provide a novel arrangement of the specimen collecting and testing apparatus for retaining the specimen thus collected having tamper-proof features.

Therefore the first aspect of the present invention is that there is provided a specimen collecting and testing apparatus for testing drug of abuse comprising:-
a) a first chamber (20) for collecting specimen having a slot (24);
b) a second chamber (30) having a puncturing means (34) adapted for receiving the specimen;
c) a third chamber (40) for testing specimen having means adapted to fasten the chamber (40) to the lid (10) and having a plurality of flanges at an inner rim (44) of the chamber (40); and
d) a lid (10) having means adapted to fasten it onto the third chamber (40);
wherein an extended circular top surface (33) of the second chamber (30) is sealed onto the inner rim (44) of the third chamber (40) and the first chamber (20) is pushed below the plurality of flanges (46) on the third chamber (40) and after the specimen is collected in the first chamber (20) the lid (10) is fastened onto the third chamber (40).

The second aspect of the present invention provides for a method for testing specimen for drug of abuse using the specimen collecting and testing apparatus comprising the steps of:
a) collecting the specimen in the first chamber (20);
b) fastening the lid (10) and the puncturing means (34) in the second chamber (30) punctures the slot (24) in the first chamber (20) thereby;
c) allowing the specimen to flow downward into the second chamber (30) gravitationally;
d) sealing the opening of the slot (24) once the urine completely flows down to the second chamber (30) by the floating member (34a);
e) once the specimen is in the second chamber (30), the specimen flows out to the third chamber (40) through the plurality of holes (35) on the end side wall of the second chamber (30) which allow the specimen to flow to the drug of abuse test strips (37) placed on the outer wall of the second chamber (30); and
f) reading immediately the test result on each drug of abuse test strip (37) through the transparent wall of the chamber.

Another further aspect of the present invention is that there is provided a specimen collecting and testing apparatus for testing drug of abuse, said apparatus is tamper-proof, adulteration proof and substitution of specimen proof comprising:- a) a first chamber (20) for collecting specimen having a slot (24);
b) a second chamber (30) having a puncturing means (34) adapted for receiving the specimen;
c) a third chamber (40) for testing specimen having means adapted to fasten the chamber (40) to the lid (10) and having a plurality of flanges at an inner rim (44) of the chamber (40); and
d) a lid (10) having means adapted to fasten it onto the third chamber (40);

wherein an extended circular top surface (33) of the second chamber (30) is sealed onto the inner rim (44) of the third chamber (40) and the first chamber (20) is pushed below the plurality of flanges (46) on the third chamber (40) and after the specimen is collected in the first chamber (20) the lid (10) is fastened onto the third chamber (40).

A final aspect of the present invention is that there is provided a method for testing specimen for drug of abuse using the specimen collecting and testing apparatus, said apparatus is tamper-proof, adulteration proof and substitution of specimen proof comprising the steps of:

a) collecting the specimen in the first chamber (20);
b) fastening the lid (10) and the puncturing means (34) in the second chamber (30) punctures the slot (24) in the first chamber (20) thereby;
c) allowing the specimen to flow downward into the second chamber (30) gravitationally;
d) sealing the opening of the slot (24) once the urine completely flows down to the second chamber (30) by the floating member (34a);
e) once the specimen is in the second chamber (30), the specimen flows out to the third chamber (40) through the plurality of holes (35) on the end side wall of the second chamber (30) which allow the specimen to flow to the drug of abuse test strips (37) placed on the outer wall of the second chamber (30); and
f) reading immediately the test result on each drug of abuse test strip (37) through the transparent wall of the chamber.

The novel features and the preferred embodiment of the present invention are now described in detail in the description below.

BRIEF DESCRIPTION OF THE DRAWINGS

The present invention can be more fully understood by referring to the following more particular description of a preferred embodiment of the invention, as illustrated in the accompanying drawings. The drawings are not necessarily to scale, instead emphasis is being placed upon illustrating principles of the invention in a clear manner.

DETAILED DESCRIPTION OF THE INVENTION

Figure 1:
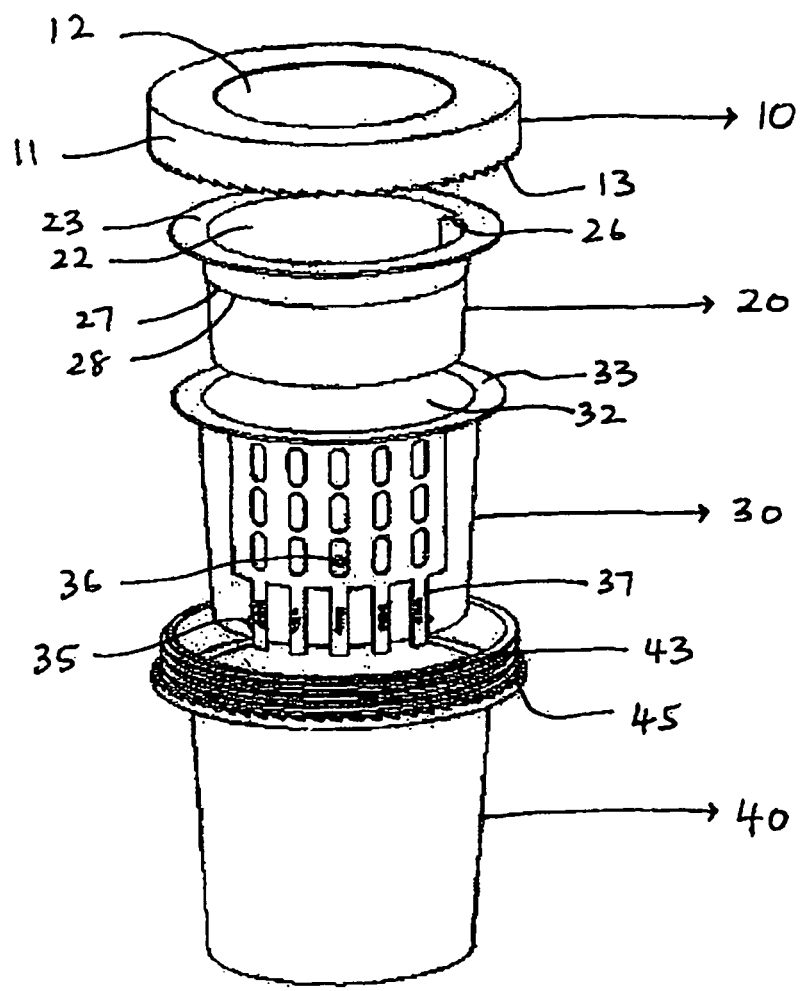
FIG. 1 shows an isometric exploded view of the specimen collecting and testing apparatus of this invention.

FIG. 1 illustrates a specimen collecting and testing apparatus according to the present invention having tamper-proof features to prevent adulteration or substitution of specimen after it has been collected for use in screening for the presence of drugs of abuse. The apparatus consists of a lid (10) having interlocking seal with gripping jaws (13) and three transparent chambers namely first chamber (20), second chamber (30) with a puncturing means (34) and third chamber (40) having an interlocking seal with gripping jaws (45). The lid (10) is independent of the chambers (20, 30 & 40). The chambers (20, 30 & 40) are arranged in a specific order and fastened by a lid (10) to form a tamper-proof specimen collecting and testing apparatus. The lid (10), first chamber (20), second chamber (30) and third chamber (40) can be of any shape. In the preferred embodiment, the lid (10), first chamber (20), second chamber (30) and third chamber (40) is cylindrical in shape. The collecting and testing apparatus can be used for testing human body fluid. However, in the present embodiment the specimen is urine.

The entire specimen collecting and testing apparatus is made from a transparent or semi-transparent material that allows easy viewing of the inside chambers. The materials used for this purpose can include but is not limited to plastic, polyurethane, polypropylene, polyvinyl chloride (PVC), wood-plastic composite, high-density polyethylene, low-density polyethylene, polycarbonate, glass, resin, alternative transparent resins namely transparent ABS (Acrylonitrile Butadiene Styrene) and transparent HIPS (High Impact Polystyrene) and acrylic. In the preferred embodiment the specimen collecting and testing apparatus is made from transparent polyvinyl chloride.

The method of fabricating the specimen collecting and testing apparatus can include but is not limited to moulding, casting, machining, extruding, forming or compounding process. In the preferred embodiment the fabrication method is injection moulding.

Figure 2:
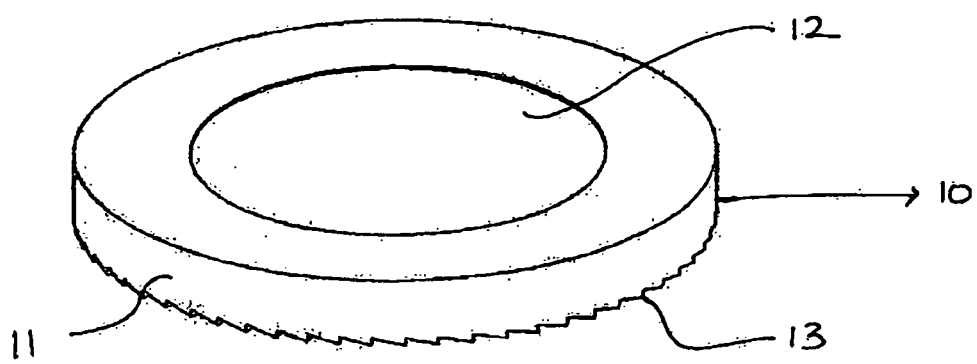
FIG. 2 shows the side view of the lid (10)

FIG. 2 shows the side view of the lid (10) having an outer rim (11) and an inner rim (12) wherein the outer rim (11) has means adapted to securely fasten the said lid (10) onto the third chamber (40). The said means adapted to securely fasten the lid (10) is an interlocking seal with gripping jaws (13) that circumference around the lid (10). However, one skilled in the art may develop other means for attaching the lid (10) to the chamber (40).

Figure 3:
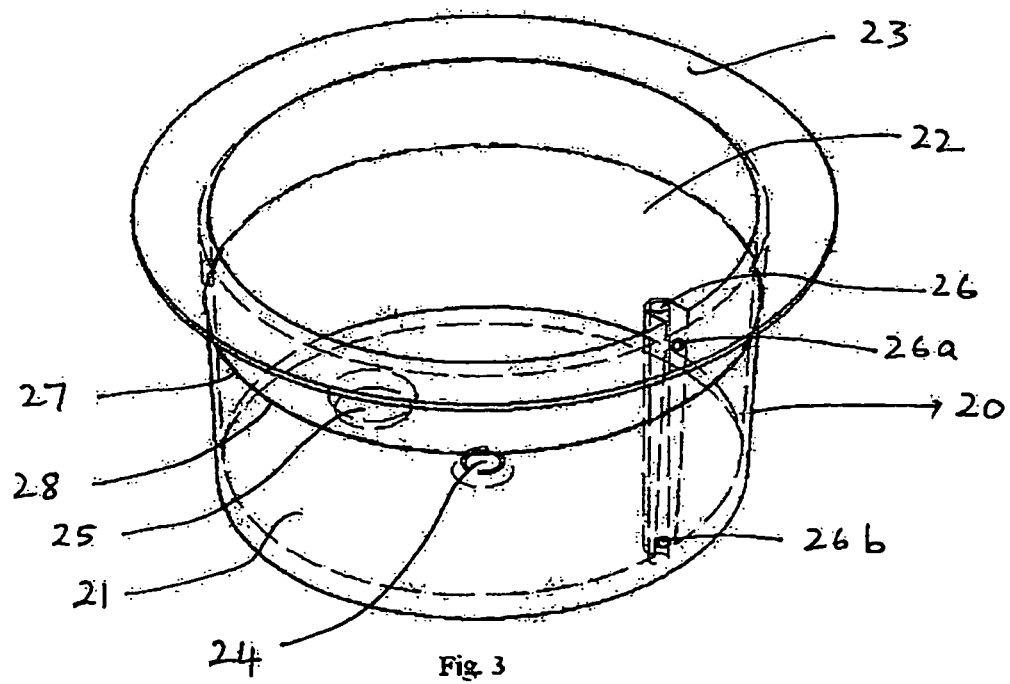
FIG. 3 shows an interior view of the first chamber (20)

FIG. 3 shows the first chamber (20) has a transparent cylindrical wall, a closed bottom end (21) and an open top end (22). The open top end (22) has an extended circular top surface (23) from the periphery which enables it to rest on top of the second chamber (30). The outside wall of the first chamber (20) has a circular groove line marking (27) and a gasket ring or rubber seal (28) below this groove line (27). The gasket ring or rubber seal (28) acts to prevent backflow of the urine specimen and the circular groove line (27) prevent the gasket ring or rubber seal (28) from moving above the groove line (27). This is one of the leak proof feature of the tamper-proof specimen collecting and testing apparatus In the center of the closed bottom end (21) of the first chamber (20) there is small slot (24) that can be punctured or pierced. Towards one side of closed bottom end (21) of the first chamber (20) there is another small indented slot (25) for allowing the specimen to be collected for confirmatory test in a certified laboratory. This is to ensure non spillage during transferring of the specimen and also contamination. A pointed object is used to puncture the said indented puncturing slot (25). Using a needle and syringe/pipette the specimen is then collected from the second chamber (30) to perform confirmatory test. There is an air release channel (26) on one side which is along the inside wall of the chamber (20) wherein the channel (26) has two breathing openings. One of the breathing opening (26a) is above the groove line (27) and the other breathing opening (26b) is below the groove line (27). These breathing openings allow any air trapped in the second chamber (30) to escape. Air can escape through the breathing opening (26b) out from the second chamber (30).

Figure 4:
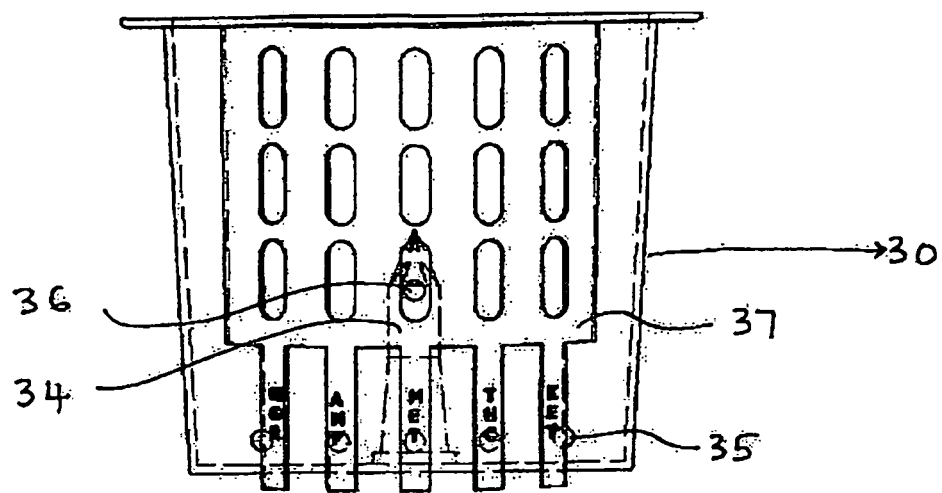
FIG. 4 shows a side view of the second chamber (30)
Figure 5:
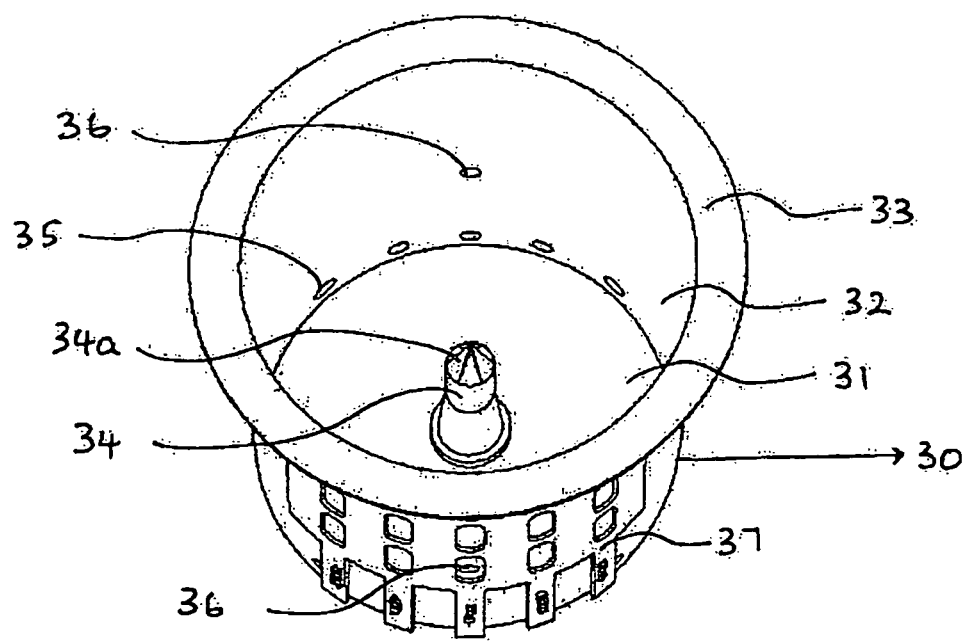
FIG. 5 shows an interior view of the second chamber (30)

FIG. 4 and FIG. 5 show that the second chamber (30) has a transparent cylindrical wall, a closed bottom end (31) and an open top end (32) wherein the open top end (32) has an extended circular top surface (33) from the periphery. The extended circular top surface (33) of the second chamber (30) is sealed onto the inner rim (44) of the third chamber (40)) to ensure there is no backflow of the specimen which is another leaf proof feature as well as tamper-proof features to prevent adulteration or substitution of the specimen.

In FIG. 5 at the center of the closed bottom end (31) of the second chamber (30), there is a vertically protruded puncturing means (34) which is one of the tamper-proofing features of the apparatus. There is a floating member (34a) proximate to the puncturing means (34). In this preferred embodiment, the floating member (34a) is on top of the puncturing means (34). The floating member (34a) is configured to seal the opening of the slot (24) in the first chamber (20) and this prevents the backflow of the specimen into the first chamber (20). The end wall near the closed bottom end (31) of the second chamber (30) has plurality of openings (35). This is to allow flow of the specimen to the third chamber (40) when the base of the first chamber (20) is pressed against the vertically protruded puncturing means (34). The drug of abuse test strips (37) is placed on the outer wall of the second chamber (30). There is also a breathing opening (36) on opposite sides of the wall of the chamber (30). This is to allow any air trapped in the third chamber (40) to be released into the second chamber (30) through the breathing opening (36). And air from the second chamber (30) can escape through the breathing opening (26b) of the first chamber (20).

Figure 6:
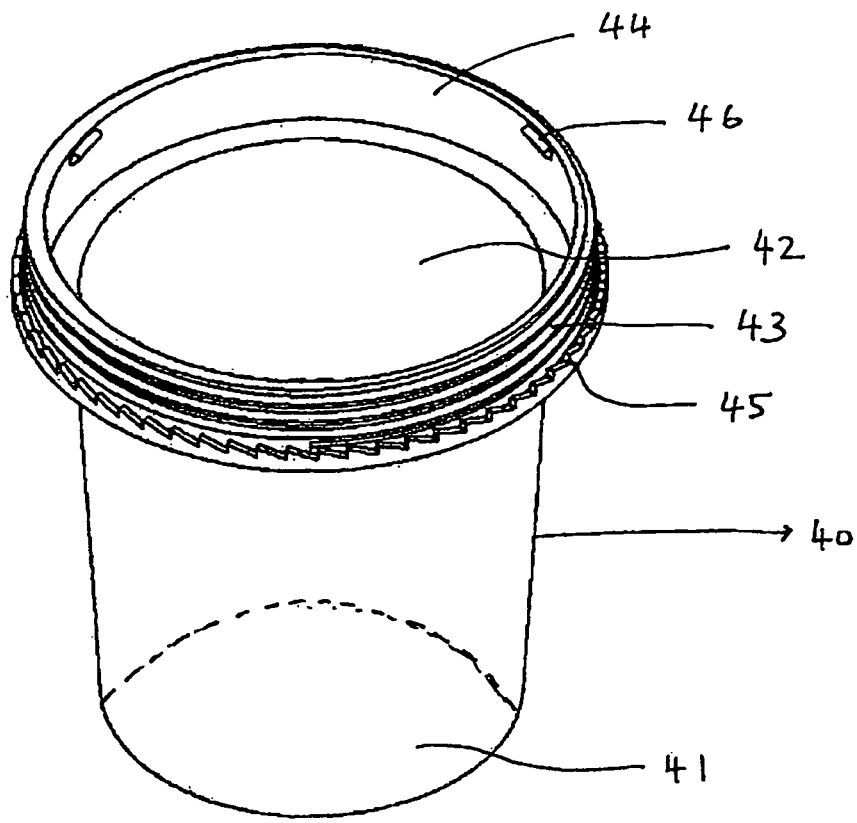
FIG. 6 shows a rear view of the third chamber (40)
Figure 7:
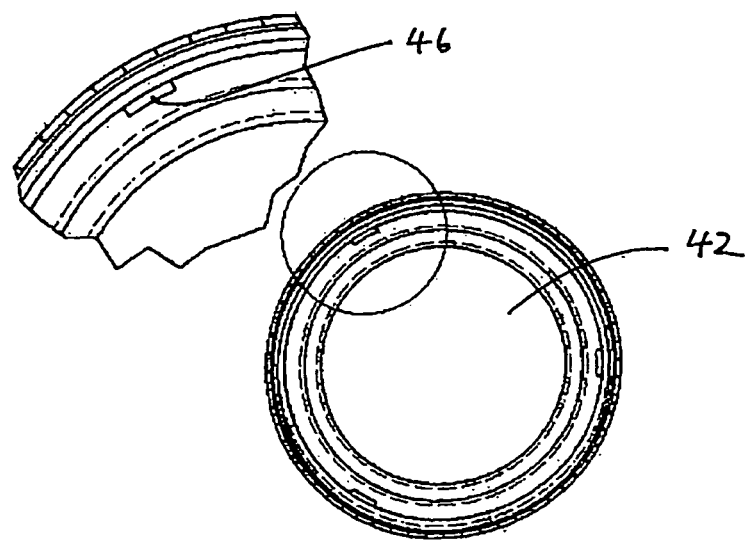
FIG. 7 shows the top view of the open top end (42) of the third chamber (40) wherein there is plurality of flanges (46) at the inner rim (44) of the said chamber (40).

FIG. 6 shows that the third chamber (40) has a cylindrical side wall, a closed bottom end (41) and an open top end (42). The open top end (42) of the third chamber (40) has an outer rim (43) and an inner rim (44). The outer rim (43) has means adapted to securely fasten the said chamber (40) to the lid (10). The said means adapted to securely fasten to the lid (10) is an interlocking seal with gripping jaws (45) that circumference around the outer rim (43). The inner rim (44) has plurality of flanges (46) as shown in FIG. 7. The first chamber (20) is pushed past the plurality of flanges (46) at the inner rim (44) of said chamber (40). This plurality of flanges (46) prevents the first chamber (20) from being removed from the assembly which is another essential feature of the tamper-proof specimen collecting and testing apparatus.

Figure 8:
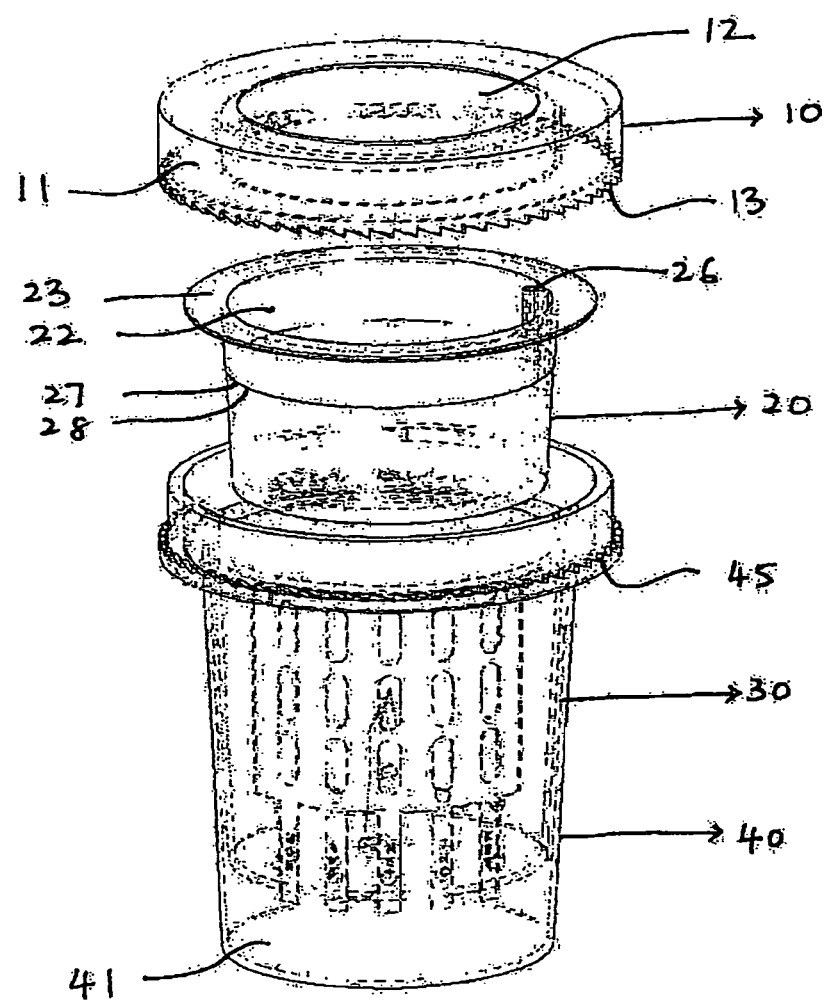
FIG. 8 shows a perspective view of the specimen collecting and testing apparatus according to the present invention wherein the extended circular top surface (33) of the second chamber (30) is sealed onto the inner rim (44) of the third chamber (40) and the first chamber (20) will be pushed past the plurality of flanges (46) at the inner rim (44) of the third chamber (40) and the chambers (20, 30 & 40) will be closed by the lid (10).

In the present embodiment as shown in FIG. 8, the preferred assembly of the specimen collecting and testing apparatus is that an extended circular top surface (33) of the second chamber (30) is sealed onto the inner rim (44) of the third chamber (40) and the first chamber (20) is sitting in the second chamber (30) after it has been pushed below the plurality of flanges (46) of the third chamber (40). The plurality of flanges (46) is configured in a way to prevent the first chamber (20) from being removed once it is pushed into the second chamber (30). Attempt to remove the first chamber (20) will break the extended circular top surface (23) of the chamber (20). The individual deposits a specimen directly into the first chamber (20). Then the chambers (20, 30, 40) are sealed with the lid (10) by fastening tightly until the interlocking seal with gripping jaws (13) is interlocked with the interlocking seal with gripping jaws (45) of the third chamber (40). The specimen will not be able to flow down to the third chamber (40) unless the interlocking seals with gripping jaws (13 and 45) from the lid (10) and third chamber (40) are completely interlocked. To unscrew the lid (10) the gripping jaws (13, 45) will be broken. This essential tamper-proof feature will ensure that the specimen collected cannot be substituted or adulterated without breaking the gripping jaws of the interlocking seal (13, 45).

The specimen flows down to the second chamber (30) when the base of the first chamber (20) is pressed against the vertically protruded puncturing means (34) in the center of the second chamber (30). This puncturing means (34) will punctures the slot (24) on the bottom of the first chamber (20) and thereby allowing the specimen collected to flow downward into the second chamber (30) gravitationally. The floating member (34a) will seal the opening of this slot (24) once the urine completely flows down to the second chamber (30). The floating member (34a) prevents any possible backflow of urine specimen into the first chamber (20).

Once the specimen is in the second chamber (30), the specimen will flows out to the third chamber (40) through the plurality of holes (35) on the end side wall of the second chamber (30). The plurality of holes (35) allow the specimen to flow to the drug of abuse test strips (37) which are placed on outer wall of the second chamber (30).

The drug of abuse test strips (37) then absorbs the specimen being tested and provides a reading of negative or positive, as the case maybe. Negative being two distinct red to purple lines on the control region and test region of the drug of abuse test strips (37) accordingly and positive being only one line appearing on the control region.

If the specimen should test "positive" to indicate the presence of a drug in the specimen, it is then necessary to send the specimen for confirmatory test done in a certified laboratory. During the transfer of the specimen it may be that vigorous shaking of the container causes spillage of the specimen or backflow of the specimen. But with the lid (10) tightly interlocking the three chambers (20, 30, 40), the chambers (20, 30, 40) are leak proof and backflow of the specimen from the third chamber (40) is not possible as the specimen flows gravitationally down from the plurality of holes (35) of the second chamber (30). Additionally, the specimen is not spilled or contaminated if the lid (10) is opened for confirmatory test in a certified laboratory. Once the lid (10) is opened exposing the first chamber (20), a pointed object is to be used to puncture the indented small slot (25). Using a needle and syringe/pipette the specimen is then collected from the second chamber (30) to perform said confirmatory test.

As an added tamper proof security feature of the specimen collecting and testing apparatus, there is a specific serial number on the heat sealed lid (10) that matches with the serial number on the second chamber (30). A tear off serial number which matches the heat sealed serial number is also attached on the outside wall of the first chamber (20). This tear off serial number is to be placed on the specific specimen test request form which is being sent to the laboratory for sample confirmation test. This will allow better control on the movement and corresponding connectivity of the specimen to the specific individual.

Thus, this present invention has been described and illustrated by reference to specific embodiments. It should be apparent, however, to those skilled in the art that various changes and modifications besides those described are possible without departing from the inventive concepts herein. The present invention, therefore, is not to be restricted except in the spirit of the appended claims.

What is claimed is:

1. A specimen collecting and testing apparatus for testing drug of abuse comprising:
   a) a first chamber for collecting specimen, the first chamber having a puncturable region that forms a slot when punctured, the first chamber also having a radially extending circular top surface;
   b) a second chamber having a puncturing means, the second chamber being adapted for receiving the specimen;
   c) a third chamber for testing specimen having a plurality of flanges at an inner rim of the third chamber, the plurality of flanges being positioned at the same vertical height on an inside surface of the third chamber; and
   d) a lid having means adapted to fasten the lid onto the third chamber, the third chamber having means adapted to fasten the third chamber to the lid;
   wherein:
   a radially extending circular top surface of the second chamber is sealed onto the inner rim of the third chamber, and
   with the second chamber received within the third chamber and the first chamber received within the second chamber below the plurality of flanges, fastening the lid onto the third chamber causes the puncturing means to puncture the puncturable region in the first chamber,
   and wherein removal of the first chamber from the third chamber is prohibited due to abutment of the radially extending circular top surface of the first chamber against a bottom surface of the plurality of flanges such that an attempt to remove the first chamber from the third chamber will break the radially extending circular top surface of the first chamber.

2. The specimen collecting and testing apparatus according to claim 1, further comprising a floating member proximate to the puncturing means, said floating member being configured to seal the opening of the slot in the first chamber and to prevent backflow of the specimen to the first chamber.

3. The specimen collecting and testing apparatus according to claim 1, wherein the means adapted to fasten the lid to the third chamber comprises gripping jaws and the means of the third chamber comprises gripping jaws, and wherein when the gripping jaws of the lid are interlocked with the gripping jaws of the third chamber, unscrewing the lid will break the gripping jaws or the lid and/or the gripping jaws of the third chamber.

4. The specimen collecting and testing apparatus according to claim 1, wherein the lid is independent of the first, second and third chambers.

5. The specimen collecting and testing apparatus according to claim 1, wherein the lid, first chamber, second chamber and third chamber can be of any shape.

6. The specimen collecting and testing apparatus according to claim 5, wherein the lid, first chamber, second chamber and third chamber are cylindrical in shape.

7. A method for testing specimen for drugs of abuse using the specimen collecting and testing apparatus as claimed in claim 1 comprising the steps of:
   a) collecting the specimen in the first chamber;
   b) fastening the lid onto the third chamber to cause the puncturing means to puncture the puncturable region to form the slot in the first chamber;
   c) allowing the specimen to flow downward into the second chamber gravitationally;
   d) sealing the opening of the slot once the specimen completely flows down to the second chamber by the floating member;
   e) once the specimen is in the second chamber, the specimen flows out to the third chamber through a plurality of holes of the second chamber and allowing the specimen to flow to at least one drug of abuse test strip placed on an outer wall of the second chamber; and
   f) reading a test result on the at least one drug of abuse test strip through a transparent wall of the third chamber.

8. The method as claimed in claim 7, wherein the specimen is human body fluid.

9. The method as claimed in claim 8, wherein the specimen is urine.

10. The method according to claim 7, wherein the specimen collecting and testing apparatus prevents tampering, adulterating or substituting the specimen after it has been collected.

11. The specimen collecting and testing apparatus according to claim 1, wherein the puncturable region comprises an indentation and is adapted to be punctured by the puncturing means to open fluid communication between the first chamber and the second chamber.

12. The specimen collecting and testing apparatus according to claim 1, wherein the second chamber is adapted to receive the first chamber such that the first chamber can be moved into the second chamber.

13. The specimen collecting and testing apparatus according to claim 1, wherein the puncturing means is attached to the second chamber.

14. The specimen collecting and testing apparatus according to claim 1, wherein the first chamber is moveable relative to the third chamber after the first chamber is moved below the plurality of flanges.

* * * * *